(12) United States Patent
Zaver et al.

(10) Patent No.: US 9,320,590 B2
(45) Date of Patent: *Apr. 26, 2016

(54) STENTS HAVING RADIOPAQUE MESH

(71) Applicant: Covidien LP, Mansfield, MA (US)

(72) Inventors: Steven G. Zaver, Plymouth, MN (US); Brian S. Carion, White Bear Lake, MN (US); Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 46 days.

This patent is subject to a terminal disclaimer.

(21) Appl. No.: 13/792,344

(22) Filed: Mar. 11, 2013

(65) Prior Publication Data

US 2013/0274849 A1 Oct. 17, 2013

Related U.S. Application Data

(63) Continuation of application No. 13/407,044, filed on Feb. 28, 2012, now Pat. No. 8,394,119, which is a continuation of application No. 11/708,651, filed on Feb. 20, 2007, now Pat. No. 8,152,833.

(60) Provisional application No. 60/775,818, filed on Feb. 22, 2006.

(51) Int. Cl.
*A61F 2/06* (2013.01)
*A61F 2/01* (2006.01)

(52) U.S. Cl.
CPC ... *A61F 2/06* (2013.01); *A61F 2/01* (2013.01); *A61F 2002/016* (2013.01);
(Continued)

(58) Field of Classification Search
CPC .......... A61F 2002/016; A61F 2002/018; A61F 2230/0006; A61F 2230/0067; A61F 2250/0018; A61F 2/01; A61F 2/06; A61F 2250/0032

USPC ......... 606/108, 194, 200; 623/1.1–1.21, 1.23, 623/1.32–1.37, 1.39, 1.49, 1.51
See application file for complete search history.

(56) References Cited

U.S. PATENT DOCUMENTS 2,919,467 A 1/1960 Mercer
4,321,711 A 3/1982 Mano
(Continued)

FOREIGN PATENT DOCUMENTS

CN 101472537 A 7/2009
EP 855170 A2 7/1998
(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.
Brilstra, et al., Treatment of Intracranial Aneurysms by Embolization with Coils: A Systematic Review, Stroke, Journal of the American Heart Association, 1999, vol. 30, pp. 470-476.
Ferguson, Gary, Physical Factors in the Initiation, Growth and Rupture of Human Intracranial Saccular Aneurysms, J. Neurosurg, Dec. 1972, vol. 37, pp. 666-667.
(Continued)

*Primary Examiner* — Ashley Fishback
(74) *Attorney, Agent, or Firm* — Mark J. Kertz, Esq.

(57) ABSTRACT

A stent including a mesh made of strands. The mesh has at least one radiopaque strand and at least one non-radiopaque strand, and the at least one radiopaque strand and the at least one non-radiopaque strand each have different diameters. Each strand has an index of wire stiffness EI, where EI is the mathematical product of the Young's modulus (E) and the second moment of area (I). The EI of all strands in the mesh is no more than five times the EI of the strand having the smallest EI of any of the strands.

31 Claims, 4 Drawing Sheets

(52) U.S. Cl.
CPC .. *A61F 2002/018* (2013.01); *A61F 2230/0006* (2013.01); *A61F 2230/0067* (2013.01); *A61F 2250/0018* (2013.01); *A61F 2250/0032* (2013.01)

(56) References Cited

U.S. PATENT DOCUMENTS

| | | |
|---|---|---|
| 4,503,569 A | 3/1985 | Dotter |
| 4,512,338 A | 4/1985 | Balko et al. |
| 4,538,622 A | 9/1985 | Samson et al. |
| 4,572,186 A | 2/1986 | Gould et al. |
| 4,580,568 A | 4/1986 | Gianturco |
| 4,655,771 A | 4/1987 | Wallsten |
| 4,681,110 A | 7/1987 | Wiktor |
| 4,733,665 A | 3/1988 | Palmaz |
| 4,743,251 A | 5/1988 | Barra |
| 4,768,507 A | 9/1988 | Fischell et al. |
| 4,776,337 A | 10/1988 | Palmaz |
| 4,856,516 A | 8/1989 | Hillstead |
| 4,954,126 A | 9/1990 | Wallsten |
| 5,011,488 A | 4/1991 | Ginsburg |
| 5,035,706 A | 7/1991 | Giantureo et al. |
| 5,041,126 A | 8/1991 | Gianturco |
| 5,061,275 A | 10/1991 | Wallsten et al. |
| 5,108,416 A | 4/1992 | Ryan et al. |
| 5,160,341 A | 11/1992 | Brenneman et al. |
| 5,180,368 A | 1/1993 | Garrison |
| 5,192,297 A | 3/1993 | Hull |
| 5,197,978 A | 3/1993 | Hess |
| 5,201,757 A | 4/1993 | Heyn et al. |
| 5,209,731 A | 5/1993 | Sterman et al. |
| 5,242,399 A | 9/1993 | Lau et al. |
| 5,246,420 A | 9/1993 | Kraus et al. |
| 5,246,445 A | 9/1993 | Yachia et al. |
| 5,344,426 A | 9/1994 | Lau et al. |
| 5,360,443 A | 11/1994 | Barone et al. |
| 5,382,259 A | 1/1995 | Phelps et al. |
| 5,401,257 A | 3/1995 | Chevalier, Jr. et al. |
| 5,405,377 A | 4/1995 | Cragg |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,507,768 A | 4/1996 | Lau et al. |
| 5,522,822 A | 6/1996 | Phelps et al. |
| 5,534,007 A | 7/1996 | St. Germain et al. |
| 5,545,208 A | 8/1996 | Wolff et al. |
| 5,546,880 A | 8/1996 | Ronyak et al. |
| 5,549,662 A | 8/1996 | Fordenbacher |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,601,593 A | 2/1997 | Freitag |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,628,788 A | 5/1997 | Pinchuk |
| 5,632,771 A | 5/1997 | Boatman et al. |
| 5,632,772 A | 5/1997 | Alcime et al. |
| 5,636,641 A | 6/1997 | Fariabi |
| 5,637,113 A | 6/1997 | Tartaglia et al. |
| 5,639,278 A | 6/1997 | Dereume et al. |
| 5,645,559 A | 7/1997 | Hachtman et al. |
| D381,932 S | 8/1997 | Walshe et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,718,159 A | 2/1998 | Thompson |
| 5,725,570 A | 3/1998 | Heath |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,746,765 A | 5/1998 | Kleshinski et al. |
| 5,749,883 A | 5/1998 | Halpern |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,810,837 A | 9/1998 | Hofmann et al. |
| 5,817,102 A | 10/1998 | Johnson et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,058 A | 10/1998 | Ravenscroft et al. |
| 5,830,229 A | 11/1998 | Konya et al. |
| 5,833,632 A | 11/1998 | Jacobsen et al. |
| 5,836,868 A | 11/1998 | Ressemann et al. |
| 5,843,168 A | 12/1998 | Dang |
| 5,868,754 A | 2/1999 | Levine et al. |
| 5,876,419 A | 3/1999 | Carpenter et al. |
| 5,888,201 A | 3/1999 | Stinson et al. |
| 5,902,266 A | 5/1999 | Leone et al. |
| 5,902,317 A | 5/1999 | Kleshinski et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,919,204 A | 7/1999 | Lukic et al. |
| 5,928,260 A | 7/1999 | Chin et al. |
| 5,944,728 A | 8/1999 | Bates |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,980,530 A | 11/1999 | Willard et al. |
| 5,980,533 A | 11/1999 | Holman |
| 6,012,277 A | 1/2000 | Prins et al. |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |
| 6,024,763 A | 2/2000 | Lenker et al. |
| 6,027,516 A | 2/2000 | Kolobow et al. |
| 6,033,436 A | 3/2000 | Steinke et al. |
| 6,039,721 A | 3/2000 | Johnson et al. |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,111 A | 5/2000 | Hieshima et al. |
| 6,074,407 A | 6/2000 | Levine et al. |
| 6,077,295 A | 6/2000 | Limon et al. |
| 6,080,191 A | 6/2000 | Summers |
| 6,083,257 A | 7/2000 | Taylor et al. |
| 6,093,199 A | 7/2000 | Brown et al. |
| 6,096,052 A | 8/2000 | Callister et al. |
| 6,102,942 A | 8/2000 | Ahari |
| 6,123,712 A | 9/2000 | Di Caprio et al. |
| 6,126,685 A | 10/2000 | Lenker et al. |
| 6,132,459 A | 10/2000 | Piplani et al. |
| 6,139,543 A | 10/2000 | Esch et al. |

(56) References Cited

U.S. PATENT DOCUMENTS

| | | |
|---|---|---|
| 6,146,415 A | 11/2000 | Fitz |
| 6,149,680 A | 11/2000 | Shelso et al. |
| 6,159,228 A | 12/2000 | Frid et al. |
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |
| 6,183,410 B1 | 2/2001 | Jacobsen et al. |
| 6,183,508 B1 | 2/2001 | Stinson et al. |
| 6,187,013 B1 | 2/2001 | Stoltze et al. |
| 6,193,708 B1 | 2/2001 | Ken et al. |
| 6,197,046 B1 | 3/2001 | Piplani et al. |
| 6,203,569 B1 | 3/2001 | Wijay |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,598 B1 | 5/2001 | Berry et al. |
| 6,235,050 B1 | 5/2001 | Quiachon et al. |
| 6,241,759 B1 | 6/2001 | Piplani et al. |
| 6,245,087 B1 | 6/2001 | Addis |
| 6,245,103 B1 | 6/2001 | Stinson |
| 6,251,132 B1 | 6/2001 | Ravenscroft et al. |
| 6,258,115 B1 | 7/2001 | Dubrul |
| 6,260,458 B1 | 7/2001 | Jacobsen et al. |
| 6,261,305 B1 | 7/2001 | Marotta et al. |
| 6,261,316 B1 | 7/2001 | Shaolian et al. |
| 6,264,671 B1 | 7/2001 | Stack et al. |
| 6,264,689 B1 | 7/2001 | Colgan et al. |
| 6,270,523 B1 | 8/2001 | Herweck et al. |
| 6,280,465 B1 | 8/2001 | Cryer |
| 6,287,331 B1 | 9/2001 | Heath |
| 6,290,721 B1 | 9/2001 | Heath |
| 6,299,636 B1 | 10/2001 | Schmitt et al. |
| 6,302,810 B2 | 10/2001 | Yokota |
| 6,302,893 B1 | 10/2001 | Limon et al. |
| 6,309,353 B1 | 10/2001 | Cheng et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,325,826 B1 | 12/2001 | Vardi et al. |
| 6,334,871 B1 | 1/2002 | Dor et al. |
| 6,336,938 B1 | 1/2002 | Kavteladze et al. |
| 6,340,367 B1 | 1/2002 | Stinson et al. |
| 6,340,368 B1 | 1/2002 | Verbeck |
| 6,342,068 B1 | 1/2002 | Thompson |
| 6,344,041 B1 | 2/2002 | Kupiecki et al. |
| 6,348,063 B1 | 2/2002 | Yassour et al. |
| 6,350,199 B1 | 2/2002 | Williams et al. |
| 6,350,278 B1 | 2/2002 | Lenker et al. |
| 6,355,051 B1 | 3/2002 | Sisskind et al. |
| 6,355,061 B1 | 3/2002 | Quiachon et al. |
| 6,364,895 B1 | 4/2002 | Greenhalgh |
| 6,368,344 B1 | 4/2002 | Fitz |
| 6,368,557 B1 | 4/2002 | Piplani et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,389,946 B1 | 5/2002 | Frid |
| 6,395,017 B1 | 5/2002 | Dwyer et al. |
| 6,395,021 B1 | 5/2002 | Hart et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,519 B1 | 7/2002 | VanDusseldorp |
| 6,416,536 B1 | 7/2002 | Yee |
| 6,419,693 B1 | 7/2002 | Fariabi |
| 6,428,489 B1 | 8/2002 | Jacobsen et al. |
| 6,440,088 B1 | 8/2002 | Jacobsen et al. |
| 6,443,971 B1 | 9/2002 | Boylan et al. |
| 6,443,979 B1 | 9/2002 | Stalker et al. |
| 6,454,999 B1 | 9/2002 | Farhangnia et al. |
| 6,468,301 B1 | 10/2002 | Amplatz et al. |
| 6,477,768 B1 | 11/2002 | Wildner |
| 6,478,778 B1 | 11/2002 | Jacobsen et al. |
| 6,482,221 B1 | 11/2002 | Hebert et al. |
| 6,488,705 B2 | 12/2002 | Schmitt et al. |
| 6,491,648 B1 | 12/2002 | Cornish et al. |
| 6,494,895 B2 | 12/2002 | Addis |
| 6,497,711 B1 | 12/2002 | Plaia et al. |
| 6,503,450 B1 | 1/2003 | Afzal et al. |
| 6,514,261 B1 | 2/2003 | Randall et al. |
| 6,514,285 B1 | 2/2003 | Pinchasik |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine et al. |
| 6,551,352 B2 | 4/2003 | Clerc et al. |
| 6,572,646 B1 | 6/2003 | Boylan et al. |
| 6,576,006 B2 | 6/2003 | Limon et al. |
| 6,582,460 B1 | 6/2003 | Cryer |
| 6,582,461 B1 | 6/2003 | Burmeister et al. |
| 6,589,273 B1 | 7/2003 | McDermott |
| 6,592,616 B1 | 7/2003 | Stack et al. |
| 6,602,271 B2 | 8/2003 | Adams et al. |
| 6,602,280 B2 | 8/2003 | Chobotov |
| 6,605,110 B2 | 8/2003 | Harrison |
| 6,613,075 B1 | 9/2003 | Healy et al. |
| 6,613,078 B1 | 9/2003 | Barone |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,652,574 B1 | 11/2003 | Jayaraman |
| 6,656,212 B2 | 12/2003 | Ravenscroft et al. |
| 6,656,218 B1 | 12/2003 | Denardo et al. |
| 6,660,024 B1 | 12/2003 | Flaherty et al. |
| 6,660,032 B2 | 12/2003 | Klumb et al. |
| 6,663,666 B1 | 12/2003 | Quiachon et al. |
| 6,666,881 B1 | 12/2003 | Richter et al. |
| 6,669,719 B2 | 12/2003 | Wallace et al. |
| 6,673,089 B1 | 1/2004 | Yassour et al. |
| 6,673,100 B2 | 1/2004 | Diaz et al. |
| 6,679,893 B1 | 1/2004 | Tran |
| 6,682,557 B1 | 1/2004 | Quiachon et al. |
| 6,685,735 B1 | 2/2004 | Ahari |
| 6,689,120 B1 | 2/2004 | Gerdts |
| 6,689,162 B1 | 2/2004 | Thompson |
| 6,699,274 B2 | 3/2004 | Stinson |
| 6,702,843 B1 | 3/2004 | Brown et al. |
| 6,709,454 B1 | 3/2004 | Cox et al. |
| 6,712,834 B2 | 3/2004 | Yassour et al. |
| 6,726,700 B1 | 4/2004 | Levine |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,746 B2 | 11/2004 | Thompson et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,899 B1 | 3/2005 | Rivelli, Jr. |

(56) References Cited

U.S. PATENT DOCUMENTS

| | | |
|---|---|---|
| 6,860,900 B2 | 3/2005 | Clerc et al. |
| 6,860,901 B1 | 3/2005 | Baker et al. |
| 6,866,677 B2 | 3/2005 | Douk et al. |
| 6,866,679 B2 | 3/2005 | Kusleika |
| 6,866,680 B2 | 3/2005 | Yassour et al. |
| 6,887,267 B2 | 5/2005 | Dworschak et al. |
| 6,890,337 B2 | 5/2005 | Feeser et al. |
| 6,893,451 B2 | 5/2005 | Cano et al. |
| 6,918,921 B2 | 7/2005 | Brady et al. |
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,962 B2 | 2/2006 | Stinson |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,041,129 B2 | 5/2006 | Rourke et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,192,434 B2 | 3/2007 | Anderson et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,438,712 B2 | 10/2008 | Chouinard |
| 7,462,192 B2 | 12/2008 | Norton et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,520,893 B2 | 4/2009 | Rivelli, Jr. |
| RE40,816 E | 6/2009 | Taylor et al. |
| 7,572,288 B2 | 8/2009 | Cox |
| 7,572,290 B2 | 8/2009 | Yodfat et al. |
| 7,588,597 B2 | 9/2009 | Frid |
| 7,695,507 B2 | 4/2010 | Rivelli, Jr. et al. |
| 7,763,011 B2 | 7/2010 | Ortiz et al. |
| 7,771,463 B2 | 8/2010 | Ton et al. |
| 7,854,760 B2 | 12/2010 | Molaei et al. |
| 7,901,447 B2 | 3/2011 | Molaei et al. |
| 7,942,925 B2 | 5/2011 | Yodfat et al. |
| 8,007,529 B2 | 8/2011 | Yan |
| 8,092,486 B2 | 1/2012 | Berrada et al. |
| 8,092,508 B2 | 1/2012 | Leynov et al. |
| 8,192,484 B2 | 6/2012 | Frid |
| 2001/0027338 A1 | 10/2001 | Greenberg |
| 2001/0044651 A1 | 11/2001 | Steinke et al. |
| 2001/0049547 A1 | 12/2001 | Moore |
| 2001/0056299 A1 | 12/2001 | Thompson |
| 2002/0004667 A1 | 1/2002 | Adams et al. |
| 2002/0007194 A1 | 1/2002 | Plowiecki |
| 2002/0029061 A1 | 3/2002 | Amplatz et al. |
| 2002/0035396 A1 | 3/2002 | Heath |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi |
| 2002/0111633 A1 | 8/2002 | Stoltze et al. |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer |
| 2003/0023299 A1 | 1/2003 | Amplatz et al. |
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0133223 A1 | 7/2004 | Weber |
| 2004/0153117 A1 | 8/2004 | Clubb et al. |
| 2004/0162606 A1 | 8/2004 | Thompson |
| 2004/0172055 A1 | 9/2004 | Huter et al. |
| 2004/0186368 A1 | 9/2004 | Ramzipoor et al. |
| 2004/0193178 A1 | 9/2004 | Nikolchev |
| 2004/0193179 A1 | 9/2004 | Nikolchev |
| 2004/0193208 A1 | 9/2004 | Talpade et al. |
| 2004/0199243 A1 | 10/2004 | Yodfat |
| 2004/0210235 A1 | 10/2004 | Deshmukh et al. |
| 2004/0215332 A1 | 10/2004 | Frid |
| 2004/0220585 A1 | 11/2004 | Nikolchev |
| 2004/0220608 A1 | 11/2004 | D'Aquanni et al. |
| 2004/0220663 A1 | 11/2004 | Rivelli, Jr. |
| 2004/0254628 A1 | 12/2004 | Nazzaro et al. |
| 2004/0260331 A1 | 12/2004 | D'Aquanni et al. |
| 2005/0004595 A1 | 1/2005 | Boyle et al. |
| 2005/0021075 A1 | 1/2005 | Bonnette et al. |
| 2005/0033407 A1 | 2/2005 | Weber et al. |
| 2005/0038447 A1 | 2/2005 | Huffmaster |
| 2005/0051243 A1 | 3/2005 | Forbes Jones et al. |
| 2005/0055047 A1 | 3/2005 | Greenhalgh |
| 2005/0059889 A1 | 3/2005 | Mayer |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |

(56) References Cited

U.S. PATENT DOCUMENTS

| | | |
|---|---|---|
| 2005/0149111 A1 | 7/2005 | Kanazawa et al. |
| 2005/0165441 A1 | 7/2005 | McGuckin et al. |
| 2005/0177186 A1 | 8/2005 | Cully et al. |
| 2005/0192620 A1 | 9/2005 | Cully et al. |
| 2005/0209672 A1 | 9/2005 | George et al. |
| 2005/0209678 A1 | 9/2005 | Henkes et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow et al. |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1 | 8/2006 | Kaufmann et al. |
| 2006/0195118 A1 | 8/2006 | Richardson |
| 2006/0206148 A1 | 9/2006 | Khairkhahan et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2007/0021816 A1 | 1/2007 | Rudin |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang |
| 2007/0077347 A1 | 4/2007 | Richter |
| 2007/0100321 A1 | 5/2007 | Rudakov et al. |
| 2007/0100414 A1 | 5/2007 | Licata et al. |
| 2007/0100430 A1 | 5/2007 | Rudakov et al. |
| 2007/0112415 A1 | 5/2007 | Bartlett |
| 2007/0119295 A1 | 5/2007 | McCullagh et al. |
| 2007/0123969 A1 | 5/2007 | Gianotti |
| 2007/0162104 A1 | 7/2007 | Frid |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng |
| 2007/0208415 A1 | 9/2007 | Grotheim et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne |
| 2007/0255388 A1 | 11/2007 | Rudakov et al. |
| 2007/0280850 A1 | 12/2007 | Carlson |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0015673 A1 | 1/2008 | Chuter |
| 2008/0033341 A1 | 2/2008 | Grad |
| 2008/0033526 A1 | 2/2008 | Atladottir et al. |
| 2008/0039930 A1 | 2/2008 | Jones et al. |
| 2008/0039933 A1 | 2/2008 | Yodfat et al. |
| 2008/0082154 A1 | 4/2008 | Tseng et al. |
| 2008/0114391 A1 | 5/2008 | Dieck et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad |
| 2008/0300667 A1 | 12/2008 | Hebert et al. |
| 2008/0300673 A1* | 12/2008 | Clerc et al. ............... A61F 2/90 632/1.15 |
| 2009/0024202 A1 | 1/2009 | Dave et al. |
| 2009/0024205 A1 | 1/2009 | Hebert et al. |
| 2009/0030496 A1 | 1/2009 | Kaufmann et al. |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso |
| 2009/0125093 A1 | 5/2009 | Hansen |
| 2009/0192536 A1 | 7/2009 | Berez et al. |
| 2009/0192587 A1 | 7/2009 | Frid |
| 2009/0198318 A1 | 8/2009 | Berez et al. |
| 2009/0270974 A1 | 10/2009 | Berez et al. |
| 2009/0287241 A1 | 11/2009 | Berez et al. |
| 2009/0287288 A1 | 11/2009 | Berez et al. |
| 2009/0288000 A1 | 11/2009 | McPherson |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0061604 A1 | 3/2010 | Nahm et al. |
| 2010/0063531 A1 | 3/2010 | Rudakov et al. |
| 2010/0076317 A1 | 3/2010 | Babic et al. |
| 2010/0152834 A1 | 6/2010 | Hannes et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |
| 2010/0179647 A1 | 7/2010 | Carpenter et al. |
| 2010/0198334 A1 | 8/2010 | Yodfat et al. |
| 2010/0204779 A1 | 8/2010 | Schuessler et al. |
| 2010/0222864 A1 | 9/2010 | Rivelli, Jr. et al. |
| 2010/0256733 A1 | 10/2010 | Schuessler |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen |
| 2011/0040372 A1 | 2/2011 | Hansen et al. |
| 2011/0046718 A1 | 2/2011 | Cattaneo et al. |
| 2011/0046720 A1 | 2/2011 | Shalev et al. |
| 2011/0166592 A1 | 7/2011 | Garcia et al. |
| 2011/0179389 A1 | 7/2011 | Douen |
| 2011/0184451 A1 | 7/2011 | Sahl |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1 | 10/2012 | Costello |
| 2012/0290067 A1 | 11/2012 | Cam et al. |
| 2012/0316638 A1 | 12/2012 | Grad et al. |
| 2012/0323309 A1 | 12/2012 | Cattaneo |
| 2013/0123901 A1 | 5/2013 | Connor et al. |
| 2013/0172975 A1 | 7/2013 | Berez et al. |

FOREIGN PATENT DOCUMENTS

| | | |
|---|---|---|
| EP | 1683541 A2 | 7/2006 |
| EP | 1485043 B1 | 7/2008 |
| EP | 1942972 A1 | 7/2008 |
| EP | 1872742 B1 | 5/2009 |
| EP | 2 078 512 A1 | 7/2009 |
| EP | 1455679 A4 | 7/2009 |
| FR | 2556210 | 6/1985 |
| FR | 2556210 B1 | 4/1988 |
| JP | 10-328216 A | 12/1998 |
| JP | 11-506686 | 6/1999 |
| JP | 11-299901 A | 11/1999 |
| JP | 2001-509412 A | 7/2001 |
| JP | 2002-253682 | 9/2002 |
| JP | 2003520103 A | 7/2003 |
| JP | 2004-049585 A | 2/2004 |
| JP | 2005-074230 A | 3/2005 |
| JP | 2006-506201 A | 2/2006 |
| JP | 2008-541832 A | 11/2008 |
| JP | 4673987 B2 | 4/2011 |

(56) References Cited

FOREIGN PATENT DOCUMENTS

| | | |
|---|---|---|
| WO | WO-88/00813 A1 | 2/1988 |
| WO | WO-95/09586 | 4/1995 |
| WO | WO-95/32757 A1 | 12/1995 |
| WO | WO-98/04211 A1 | 2/1998 |
| WO | 98/47447 A1 | 10/1998 |
| WO | WO-99/02092 A1 | 1/1999 |
| WO | 99/05977 A1 | 2/1999 |
| WO | WO-99/49812 A3 | 12/1999 |
| WO | WO-01/05331 A1 | 1/2001 |
| WO | WO-01/52771 A1 | 7/2001 |
| WO | WO-02/05729 | 1/2002 |
| WO | WO-02/47579 | 6/2002 |
| WO | WO-02/054988 | 7/2002 |
| WO | WO-02/054988 A3 | 1/2003 |
| WO | WO-03/007840 A2 | 1/2003 |
| WO | WO-03/043527 A2 | 5/2003 |
| WO | WO-03/049600 A2 | 6/2003 |
| WO | 03/057079 A1 | 7/2003 |
| WO | WO-03/073963 A2 | 9/2003 |
| WO | WO-2004/087006 A3 | 11/2004 |
| WO | WO 2005/021061 | 3/2005 |
| WO | WO-2005/023149 | 3/2005 |
| WO | WO-2005/115118 | 12/2005 |
| WO | 2006/034140 A2 | 3/2006 |
| WO | WO-2006/073745 A2 | 7/2006 |
| WO | WO-2006/127005 A1 | 11/2006 |
| WO | 20071122396 A1 | 11/2007 |
| WO | WO-2007/139689 | 12/2007 |
| WO | WO-2007/139699 A2 | 12/2007 |
| WO | 2008/005898 A2 | 1/2008 |
| WO | WO 2008/156683 | 12/2008 |
| WO | WO-2009/105710 A1 | 8/2009 |
| WO | 2010/127838 A2 | 11/2010 |
| WO | 2011/023105 A1 | 3/2011 |
| WO | 2011/134663 A2 | 11/2011 |

OTHER PUBLICATIONS

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expandable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar. 1990, Vol Supplementum 48, 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

* cited by examiner

STENTS HAVING RADIOPAQUE MESH

This application is a continuation of U.S. application Ser. No. 13/407,044, filed Feb. 28, 2012, which is a continuation of U.S. application Ser. No. 11/708,651, now U.S. Pat. No. 8,152,833, filed Feb. 20, 2007, which claims the benefit of U.S. Provisional Application No. 60/775,818, filed Feb. 22, 2006, entitled "Embolic Protection System Having Radiopaque Filter Mesh," the contents of each of which are hereby incorporated by reference herein.

FIELD OF THE INVENTION

The present invention relates to embolic protection systems, and, more particularly, to embolic protection systems for use in blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature distal to the treatment site.

To prevent embolization of debris, embolic protection devices have been developed. During a procedure such devices can be placed distal or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site. However, some anatomies present specific challenges due to the anatomical shape or configuration.

Difficulties can arise where embolic protection devices are not properly deployed within the anatomy. For example, if a device does not properly engage a lumenal wall, leaving a gap, then particulate matter entrained in a fluid in the lumen can bypass the protection device. It would be an advantage to be able to visualize whether or not there are gaps between the embolic protection device and the lumenal wall. Also, when a protection device is being advanced or withdrawn from a lumen it may engage with an obstruction. The obstruction may be a stent that has been placed in a blood vessel, an area of plaque build-up, lumen tortuosity, or other structure. The operator of the embolic protection device may need to employ different techniques to advance or withdraw the device depending on the cause of engagement. Thus, it would be advantageous for the operator to be able to visualize the exact location of the device in the lumen.

Difficulties can also arise when recovering an embolic protection device. One problem that can occur is that the embolic protection device may require excessive force during recovery, for example when drawing the device into a recovery catheter. The causes of such excessive force can vary. For example the device could be filled with embolic debris and thereby not fit into the lumen of a recovery catheter, the device may be caught on a structure such as a stent or a catheter tip, or other causes. It would be advantageous to the operator to visualize the embolic protection device so that appropriate actions can be taken so as to successfully recover the device. Further discussion of these issues is provided in U.S. Patent Publication No. 2002/0188314 A1, by Anderson et. al., entitled "Radiopaque Distal Embolic Protection Device", the contents of which are incorporated herein by reference.

The current art employs a variety of approaches to solve the problem of visualizing an embolic protection device in a patient. All of the current approaches have limitations. For example, some devices have radiopaque coatings; however coatings may become separated from the underlying substrate. Radiopaque filler materials have been employed in polymer film devices; however the fillers detract from the mechanical properties of the films and the filler/film composites, being thin, are not very visible. Strands of drawn filled tubing (DFT) have been used and have good mechanical and radiopacity characteristics; however DFT is expensive. Individual strands of radiopaque wire, such as platinum, gold, tungsten, and their alloys have good radiopacity but can have unsuitable strength or elastic yield limits, and when comprising a portion of the wires in a woven structure such as a braid, can alter the braid wire spacing in the vicinity of the strand of radiopaque wire due to differing mechanical properties compared to neighboring non-radiopaque wires. For some filter devices, uniform wire spacing is desired and altered braid wire spacing can cause unacceptably large pores in the braid.

Accordingly, a need exists for an embolic protection device having improved radiopacity that is inexpensive, durable, provides visibility to the appropriate regions of the device, and which uses technology that does not compromise the performance of the device.

SUMMARY OF THE INVENTION

According to one aspect of the present invention, an embolic protection device comprises a woven mesh comprising radiopaque and non-radiopaque wires. The mechanical properties of the radiopaque wires are selected to match the mechanical properties of the non-radiopaque wires. The non-radiopaque wires can be superelastic. The radiopaque wires are woven into pre-programmed locations so that after processing the woven mesh into a device the radiopaque wires will concentrate at a preferred location within the device. A method is provided in which the device operator visualizes the radiopaque wires so as to guide how the device is utilized in a patient.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, wherein the filter element comprises a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand.

The invention provides a method of deploying a device for filtering emboli from blood flowing through a lumen defined by the walls of a vessel in a patient's body comprising: providing the device for filtering emboli, the device comprising a filter element being expandable from a collapsed configuration when the filter element is restrained to an expanded configuration when the filter element is unrestrained, wherein the filter element comprises a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand; delivering the device percutaneously to a region of interest in the lumen of the patient's body; and using fluoroscopy to visualize the filter element in the lumen of the patient's body.

The invention provides a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand.

It is to be understood that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

DETAILED DESCRIPTION OF THE INVENTION

Figure 1A:
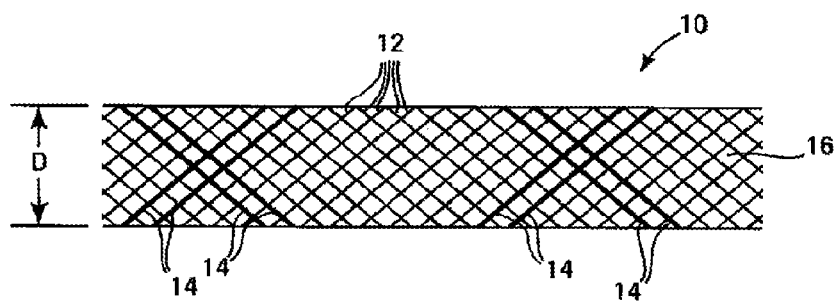
FIGS. 1A to 1C illustrate conceptually a partial plan view of braided tubular mesh having radiopaque and non-radiopaque wires in accordance with the present invention.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, wherein the filter element comprises a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand.

In one embodiment, the device further comprises an elongate support member and the filter element is carried on a portion of the elongate support member. In another embodiment, the filter element has proximal and distal portions and a central portion, the filter element having a shape in the expanded configuration which defines a cavity having a proximal facing opening. In one embodiment, the filter element has a proximal facing opening portion and this portion is radiopaque.

The filter element may be self-expanding or self-contracting. The mesh may be tubular and/or braided. In one embodiment, each strand has a round cross-section. In another embodiment, the mesh comprises only two types of strands, a first type being a radiopaque strand and having a diameter D1 and a second type being a non-radiopaque strand and having a diameter D2. In one embodiment, the Young's modulus of the radiopaque strand and the Young's modulus of the non-radiopaque strand differ by 10 percent or more. In another embodiment, the Young's modulus of the radiopaque strand and the Young's modulus of the non-radiopaque strand differ by 20 percent or more.

In one embodiment, the mesh comprises more radiopaque strands than non-radiopaque strands. In another embodiment, the mesh comprises more non-radiopaque strands than radiopaque strands. In embodiments of the invention, the largest EI of a strand is no more than four times the smallest EI of a strand, the largest EI of a strand is no more than two times the smallest EI of a strand, the largest EI of a strand is no more than 1.5 times the smallest EI of a strand, or the largest EI of a strand is no more than 1.3 times the smallest EI of a strand.

In embodiments of the invention, the mesh comprises pores and when the mesh is at rest in free space no pore has an area more than five times the mesh pore size, when the mesh is at rest in free space no pore has an area more than four times the mesh pore size, when the mesh is at rest in free space no pore has an area more than three times the mesh pore size, when the mesh is at rest in free space no pore has an area more than two times the mesh pore size, when the mesh is at rest in free space no pore has an area more than 1.5 times the mesh pore size, or when the mesh is at rest in free space no pore has an area more than 1.2 times the mesh pore size. The mesh pore size is the average area of five pores serially adjacent to the pore.

In embodiments of the invention, the mesh comprises at least two types of strands, each strand having a round cross-section, a first type of strand being a radiopaque strand and having a diameter D1 and a second type of strand being a non-radiopaque strand and having a diameter D2, diameter D1 being larger than diameter D2, wherein the mesh comprises pores and when the mesh is at rest in free space no pore adjacent to a strand having a diameter D1 has an area more than five times the mesh pore size, the mesh pore size being the average area of five pores serially adjacent to the pore. In other related embodiments, when the mesh is at rest in free space no pore adjacent to a strand having a diameter D1 has an area more than four times the mesh pore size, more than three times the mesh pore size, more than two times the mesh pore size, more than 1.5 times the mesh pore size, or more than 1.2 times the mesh pore size.

In one embodiment, the at least one radiopaque strand is made of homogeneous metal or metal alloy. In another embodiment, the at least one radiopaque strand is selected from the group consisting of strands made of gold, platinum, tungsten, tantalum, and alloys thereof. Other radiopaque substances may be used. In an embodiment, the at least one non-radiopaque strand is made of metal. In one embodiment, the at least one non-radiopaque strand is selected from the group consisting of strands made of stainless steel and nitinol. Other non-radiopaque substances may be used. In one embodiment, the at least one non-radiopaque strand is superelastic.

In embodiments of the invention, the largest diameter of a strand is no more than five times the smallest diameter of a strand, the largest diameter of a strand is no more than four times the smallest diameter of a strand, the largest diameter of a strand is no more than two times the smallest diameter of a strand, or the largest diameter of a strand is no more than 1.5 times the smallest diameter of a strand. In one embodiment, the largest diameter of a strand is no more than two times the smallest diameter of a strand, and the largest EI of a strand is no more than two times the smallest EI of a strand.

In one embodiment, the at least one radiopaque strand is a monofilament. In one embodiment, the at least one non-radiopaque strand is a monofilament. In another embodiment, the mesh comprises only two types of strands, a first type being a radiopaque strand and having a diameter D1 and a second type being a non-radiopaque strand and having a diameter D2, and both the first and second types of strands are monofilaments. In one embodiment, the at least one radiopaque strand is a multifilament wire. In another embodiment, at least one strand is a monofilament wire from which some material has been removed in the form of slots. In one embodiment, the at least one non-radiopaque strand is made of nitinol.

The invention provides a method of deploying a device for filtering emboli from blood flowing through a lumen defined by the walls of a vessel in a patient's body comprising: providing the device for filtering emboli, the device comprising a filter element being expandable from a collapsed configuration when the filter element is restrained to an expanded configuration when the filter element is unrestrained, wherein the filter element comprises a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand; delivering the device percutaneously to a region of interest in the lumen of the patient's body; and using fluoroscopy to visualize the filter element in the lumen of the patient's body. The device used in this method can be any of the embodiments described herein. In one embodiment, the filter element has proximal and distal portions and a central portion, the filter element having a shape in the expanded configuration which defines a cavity having a proximal facing opening, the filter element has a proximal facing opening portion and this portion is radiopaque, and the proximal facing opening portion of the filter element is visualized to confirm that this portion is adequately deployed against the walls of the vessel.

The invention provides a mesh comprising strands, each strand having a diameter, the mesh comprising at least one radiopaque strand and at least one non-radiopaque strand, and wherein each strand has an index of wire stiffness EI, where EI is the mathematical product of the Young's modulus (E) and the second moment of area (I), and wherein the largest EI of a strand is no more than five times the smallest EI of a strand. The mesh can be any of the embodiments described herein in connection with the mesh that is part of the device for filtering emboli.

In the discussion below the invention is described using as examples filters comprised of braided metal strands. It is to be understood that the invention is not limited to the examples below. For example, the mesh of the invention can be comprised of strands that are woven, non-woven, or knitted to form the mesh. The mesh can have uniform strand spacing so as to define a structure with relatively uniformly sized openings between strands or can have variable strand spacing so as to define a structure with varied size openings between strands. The mesh can be coated with an elastic polymer film in whole or in part, or with another material, so as to reduce in size or eliminate the openings between strands. The coated mesh may be partially or totally occlusive to flow of fluid or particles therethrough. In some embodiments the metal strands may be superelastic alloys comprised of radiopaque alloy constituents. In some preferred embodiments a metal strand is comprised of nickel-titanium-platinum or nickel-titanium-tantalum alloy. In addition, some or all of the strands may be comprised of materials other than metal including but not limited to engineering polymers such as PEEK (polyetheretherketone), liquid crystal, polyamide, or polyester; ceramics; glass-ceramics; metallic glasses; or other materials known in the art. In some embodiments the aforementioned materials can be comprised of radiopaque filler materials. In some embodiments the strands are homogeneous in the sense that they are not comprised of separate layers. It is further understood that the cross section of some or all of the strands can be round, ovoid, square, rectangular, triangular, irregular, symmetrical, non-symmetrical, or other shapes.

Figure 1B:
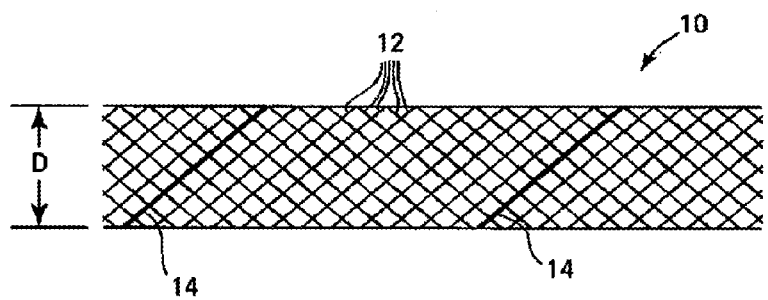
Figure 1C:
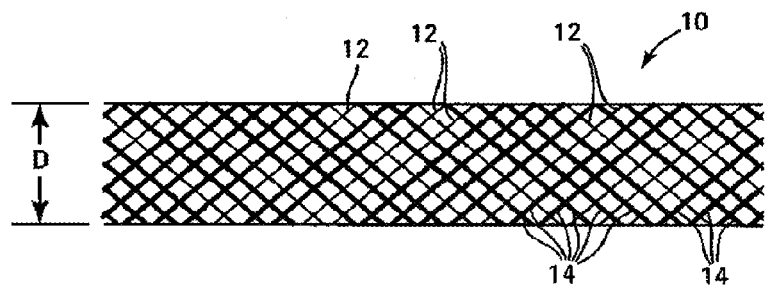

FIGS. 1A to 1C illustrate conceptually partial plan views of braided meshes having radiopaque and non-radiopaque wires in accordance with the present invention. For clarity only the braided wires along half of the braided perimeter of the tube are shown. Braided wires arranged below the illustrated wires are not shown. Also for clarity the radiopaque wires in FIGS. IA to IC are shown as having slightly increased diameter as compared to non-radiopaque wires, although it is understood that the relative sizes of the radiopaque and non-radiopaque filaments may not be as illustrated and generally will be determined according to the teachings below. Further, strands are generally illustrated as intersecting at angles of approximately 900, although it is understood that within the scope of the invention strands can intersect or overlap at any angle.

In FIG. IA braided tubular mesh 10 is comprised of interwoven wires 12 and 14. Non-radiopaque wires 12 comprise the majority of the wires and two sets of adjacent pairs of radiopaque wires 14 are interwoven with the non-radiopaque wires 12. Braided tubular mesh 10 has a number of pores 16 defined by the wires, and each pore has a size, the pore size defined as the area bounded by the wires forming the perimeter of the pore. Braided tubular mesh 10 can be formed of a variety of materials. Metal wires are preferred, and superelastic nitinol is particularly preferred for the non-radiopaque wires 12. Braided tubular mesh 10 has a diameter D, which is the diameter of the braided tubular mesh at rest in free space. Diameter D is determined by braiding processing parameters and wire diameters used. Heat treatments may be used to help stabilize diameter D, especially when wire materials such as nitinol are used. A braid comprised of nitinol wire is typically heat set at 400 to 600° C. for 1 to 60 minutes to stabilize the braid diameter. In a preferred embodiment nitinol wire is heat set at 425° C. for 20 minutes to stabilize the braid diameter. Non-nitinol wires may be annealed at temperatures that will stress relieve or even recrystallize the materials in order to stabilize the tubular braid diameter. It is understood that self-expanding or self-contracting devices can be comprised of braided tubular mesh 10. Self-expanding devices are devices in which, during use, braided tubular mesh 10 is compressed and subsequently allowed to expand without application of forces external to the mesh for causing expansion. Self-contracting devices are devices in which, during use, braided tubular mesh 10 is expanded and subsequently allowed to contract without application of forces external to the mesh for causing contraction. It is advantageous to construct self-expanding or self-contracting devices at least in part from wires that have elastic strain limits higher than the elastic strains generated in the wires during use of these devices, and to process the wires so as to retain or enhance the elastic strain limits of the wires chosen. Devices which are neither self-expanding nor self-contracting may also be comprised of braided tubular mesh 10. Devices of the invention may also be comprised of braided tubular mesh or strands which deform upon expansion or contraction. The strands of such devices may be processed or chosen such that the elastic strain limit of the strands are less than the elastic strains generated in the strand during use of the device.

FIG. 1B illustrates braided tubular mesh 10 comprised of a single radiopaque wire 14 interwoven with non-radiopaque wires 12 and FIG. 1C illustrates braided tubular mesh 10 comprised primarily of radiopaque wires 14 interwoven with a minority of non-radiopaque wires 12. It is understood that multiple combinations of interwoven radiopaque and non-radiopaque wires 14 and 12 are possible within the scope of the invention, and that the number, proportion, and positioning of radiopaque and non-radiopaque wires within the mesh will be chosen based on the desired device functional and other requirements.

Figure 2:
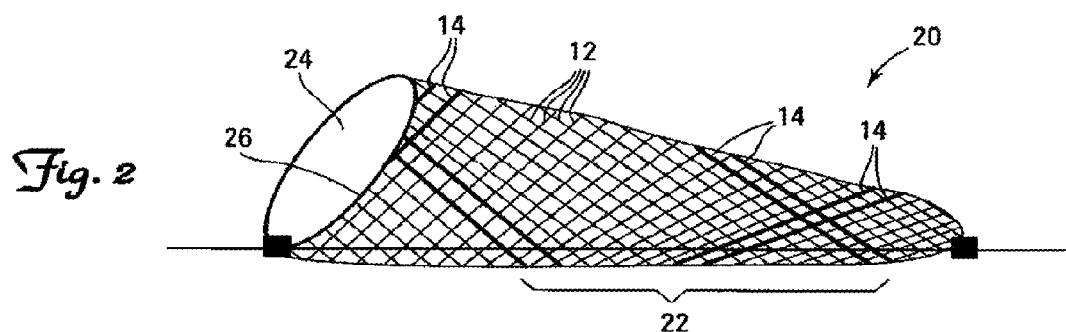
FIG. 2 illustrates conceptually a side view of a filter formed from braided tubular mesh in accordance with the present invention.

FIG. 2 illustrates conceptually a side view of filter 20 formed from a braided tubular mesh 10 comprised of interwoven radiopaque and non-radiopaque wires 12 and 14 in accordance with the present invention. For clarity the wires on the back side of the filter are not shown. Filters similar to that shown in FIG. 2 can be made by enlarging a pore in the side wall of the braid using a tapered mandrel and stabilized in the desired shape by heat treating on a mandrel. Processing details for making a filter using these methods are disclosed in U.S. Pat. No. 6,325,815 B1 to Kusleika et al., entitled "Temporary Vascular Filter", the contents of which are incorporated herein by reference. In filter 20, radiopaque wires 14 are bunched at the opening of the filter, providing improved visibility under fluoroscopy of the perimeter 26 of mouth 24 of the filter. In an alternate embodiment radiopaque wires 14 are bunched distal to mouth 24 of the filter, providing improved visibility under fluoroscopy of the portion of the filter apposing a vessel wall during use. Radiopaque wires 14 also extend throughout the body 22 of the filter mesh, providing visibility under fluoroscopy to the body of the filter.

Figure 3:
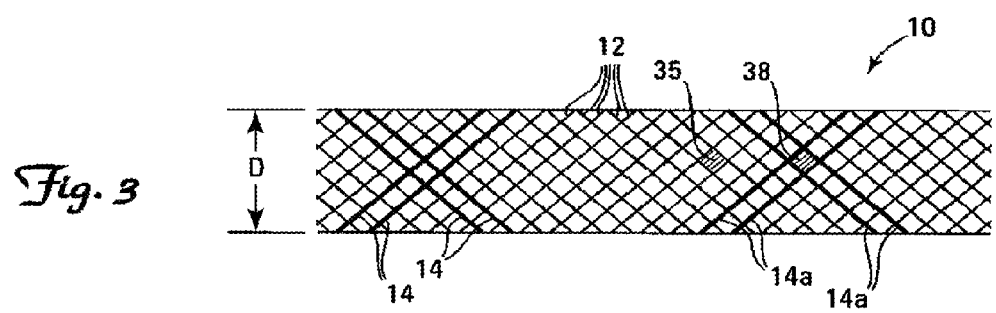
FIG. 3 illustrates conceptually a method for forming a filter from braided tubular mesh in accordance with the present invention.

FIG. 3 illustrates conceptually a method for forming filter 20 from braided tubular mesh 10 comprised of interwoven radiopaque and non-radiopaque wires 12 and 14 in accordance with the present invention. Pore 35 is chosen as the pore to enlarge into mouth 24 of filter 20. Pore 35 is chosen specifically such that radiopaque wires 14a will be bunched along the perimeter 26 of filter mouth 24 during the filter forming process. In FIG. 3, pore 35 is located 3 pores from the intersecting pore 38 of radiopaque filaments 14a. In one example, braided tubular mesh 10 is comprised of 36 wires and has a diameter D of 3 mm before forming into filter 20. Two pairs of radiopaque wires 14a are interwoven into tubular mesh 10 as illustrated in FIG. 3, and the remaining 32 wires are non-radiopaque nitinol. Pore 35 is located 8 pores from intersecting pore 38 of radiopaque filaments 14a. In another example, braided tubular mesh 10 is comprised of 72 wires and has a diameter D of 7 mm before forming into filter 20. Two pairs of radiopaque wires 14a are interwoven into tubular mesh 10 as illustrated in FIG. 3, and the remaining 68 wires are non-radiopaque. Pore 35 is located 15 pores from intersecting pore 38 of radiopaque filaments 14a. It is understood that the location chosen for piercing braided tubular mesh 10 comprised of interwoven radiopaque and non-radiopaque wires 12 and 14 will vary within the scope of the invention and will depend on the application contemplated and results desired.

Figure 4A:
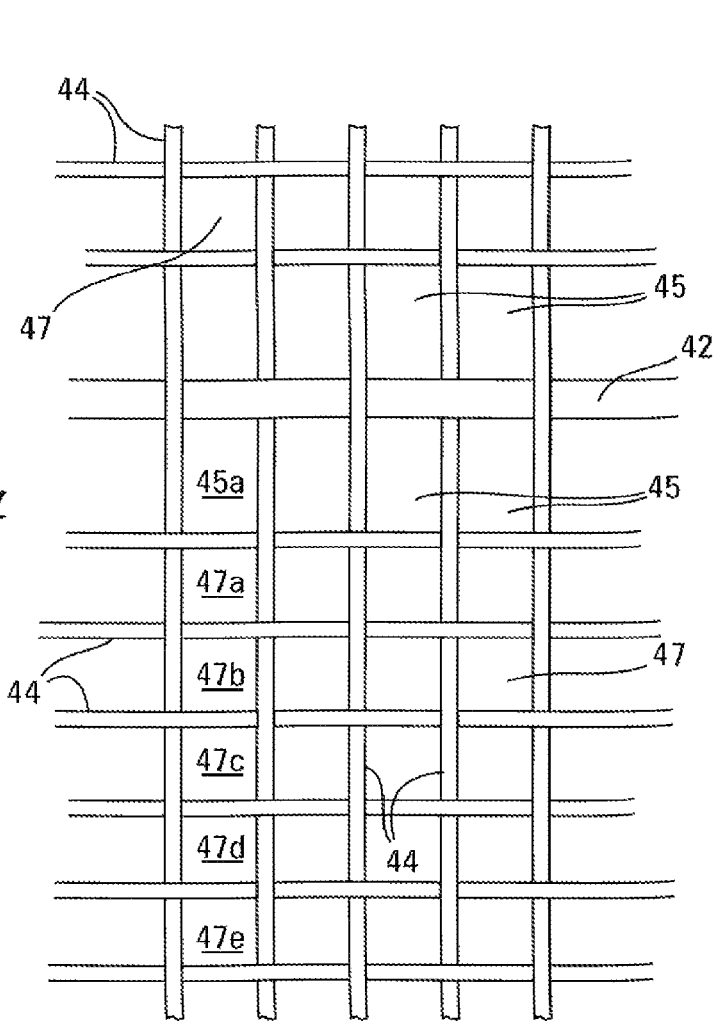
FIGS. 4A and 4B illustrate conceptually plan views of braided mesh in accordance with the present invention.

When adding radiopaque wires to a mesh comprised primarily of non-radiopaque wires it is often desired to increase the diameter of the radiopaque wire relative to the diameter of the non-radiopaque wire so as to increase the visibility of the radiopaque wire under fluoroscopy. FIG. 4A illustrates the effect of adding a larger wire 42 to a mesh 40, wherein the pore sizes 45 adjacent to the larger wires are increased in area as compared to pore sizes 47 in the portion of the mesh comprised of smaller wires 44 due to the presence of the larger wire 42 relative to the adjacent smaller wires 44 in the mesh. For certain applications, including some filter devices, large pores in the braid can be unacceptable because the large pores will allow large emboli to pass through the filter.

Figure 4B:
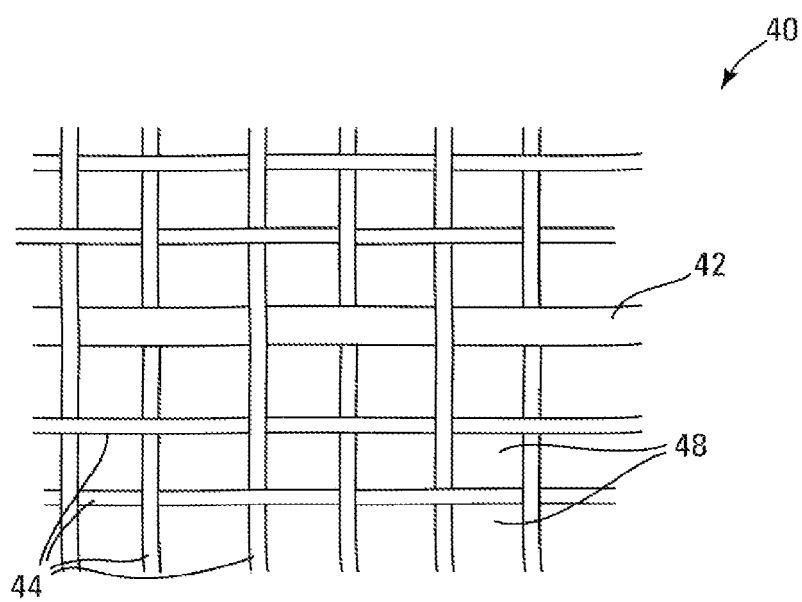

FIG. 4B illustrates braided tubular mesh 40 comprised of a large wire 42 and multiple smaller wires 44 having uniformly sized pores 48, a configuration preferred for filtering applications such as for distal embolic protection devices. The uniformly sized pores illustrated in FIG. 4B are achieved by using similar stiffness wires in the mesh. A useful index of wire stiffness is EI, where E is the Young's modulus of the wire material, I is the second moment of area of the wire, and EI is the mathematical product of the two. In a preferred embodiment of the device, the largest EI of wires used in the device is no more than 5 times the smallest EI of wires used in the device. In a more preferred embodiment of the device, the largest EI of wires used in the device is no more than 4 times the smallest EI of wires used in the device. In a further preferred embodiment of the device, the largest EI of wires used in the device is no more than 2 times the smallest EI of wires used in the device. In a further preferred embodiment of the device, the largest EI of wires used in the device is no more than 1.5 times the smallest EI of wires used in the device. In a further preferred embodiment of the device, the largest EI of wires used in the device is no more than 1.3 times the smallest EI of wires used in the device.

Referring again to FIG. 4A, the area of pore 45a adjacent to large wire 42 is much greater than the average area of the five pores 47a, 47b, 47c, 47d, and 47e serially adjacent to pore 45a. For convenience we hereby define the average area of the five pores 47a, 47b, 47c, 47d, and 47e serially adjacent to pore 45a as the mesh pore size. This definition allows us to apply the inventive teachings herein to various filter shapes with varying pore sizes, including tapered filters where the pore size varies along the length of the filter, such as the filter illustrated in FIG. 2. In a preferred embodiment of the mesh at rest in free space, the size of pore 45a adjacent to large wire 42 is no more than 5 times larger than the mesh pore size. In a more preferred embodiment of the mesh, the size of pore 45a adjacent to large wire 42 in the mesh at rest in free space is no more than 4 times larger than the mesh pore size. In a further preferred embodiment of the mesh, the size of pore 45a adjacent to large wire 42 in the mesh at rest in free space is no more than 3 times larger than the mesh pore size. In a further preferred embodiment of the mesh, the size of pore 45a adjacent to large wire 42 in the mesh at rest in free space is no more than 2 times larger than the mesh pore size. In a further preferred embodiment of the mesh, the size of pore 45a adjacent to large wire 42 in the mesh at rest in free space is no more than 1.5 times larger than the mesh pore size. In a further preferred embodiment of the mesh, the size of pore 45a adjacent to large wire 42 in the mesh at rest in free space is no more than 1.2 times larger than the mesh pore size.

Figure 5A:
FIGS. 5A to 5E illustrate cross sectional or side views of wires in accordance with the present invention.

To achieve the uniform pore size illustrated in FIG. 4B various approaches can be used to match wire stiffnesses. In one embodiment a tubular braided mesh of monofilament 52 (see FIG. 5A) stainless steel wires incorporates an interwoven monofilament wire having a larger diameter than the stainless steel wires with the Young's modulus of the interwoven larger wire less than that of stainless steel. Suitable choices of material for the larger wire include gold and platinum (see Table I below). The lower modulus of gold and platinum relative to stainless steel will offset the larger diameter of the radiopaque wire such that the calculated EI's of the radiopaque and non-radiopaque wires will be equal or similar.

TABLE 1

| Material | Young's Modulus, E (GPa) |
| --- | --- |
| Gold | 78 |
| Nitinol (Austenitic) | 75-83 |
| Platinum | 168 |
| Tungsten | 411 |
| Tantalum | 186 |
| Stainless Steel | 199 |

Figure 5B:

In an alternate embodiment, multifilament wires 53 can be used (see FIG. 5B). The diameter of each individual filament 54 of a multifilament wire is smaller than the overall diameter of the wire 53 and this allows higher modulus materials to be incorporated into some or all of the filaments 54 of a larger multifilament wire 53. For example, braided tubular mesh comprised of nitinol monofilament wires could incorporate one or more interwoven multifilament wires comprised of gold, platinum, tungsten, tantalum, or other radiopaque materials. In one embodiment of a multifilament wire more than one filament is twisted into a helical shape around a central filament. In another embodiment of multifilament wire 53 individual monofilaments are interwoven into the braid adjacent to each other as shown in FIG. 5E. It is understood that many other combinations of filaments can be devised by one skilled in the art within the scope of the invention.

Figure 5C:
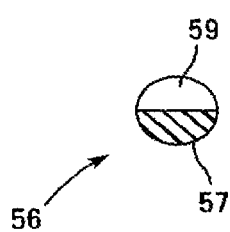
Figure 5D:
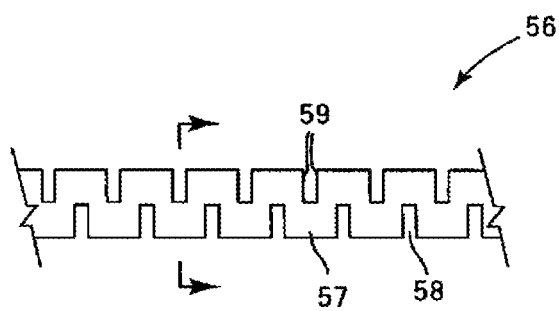
Figure 5E:
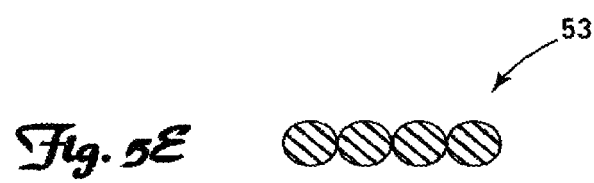

In a further embodiment, FIGS. 5C and 5D illustrate slotted wire 56 in which monofilament wire 57 has had material removed in the form of slots 58, for example by grinding. Slots 58 have opposing faces 59 and due to material having been removed from the perimeter of the wire to form slots 58 the overall modulus of wire 56 is reduced.

One example of deriving uniform pore size by matching wire stiffnesses is as follows. Tubular braided mesh is comprised of 36 Nitinol monofilament wires of 0.003" (0.0076 cm) diameter. It is desired to improve the visibility of the mesh by substituting a monofilament circular cross section tungsten wire for one of the nitinol wires, and to do so without significantly changing the pore size of the mesh. The appropriate diameter of the tungsten wire is calculated as shown below.

$$1/\rho = M/(E \times I)$$

Where $\rho$=the density of the material in bending, M=the bending moment, and E & I are as defined above. Equating the bending moments of nitinol and tungsten wires yields:

$$(E_w \times I_w)/\rho_w = M = (E_{NiTi} \times I_{NiTi})/\rho_{NiTi} \text{ and } I = (\pi d^2 L^3 \rho)/(48g)$$

Where $\pi$=3.14159, d=monofilament diameter, L=the unsupported transverse length of the filament, and g=the gravitational constant By Combining Terms:

$$E_w \times (\pi d_w^2 L_w^3 \rho_w)/(48 g \rho_w) = E_{NiTi} \times (1 t d_{NiTi}^2 L_{NiTi}^3 \rho_{NiTi})/(48 g \rho_{NiTi}) \text{ and by eliminating like terms:}$$

$$E_w \times d_w = E_{NiTi} \times d_{NiTi}^2$$

Substituting known values and solving for $d_w$ yields $$d_w = 0.0013" (0.0033 \text{ cm})$$

In another example, the appropriate diameter of gold wire to be substituted into the mesh, using the same calculation as above except substituting into the equations the material parameters of gold in place of the parameters of tungsten, would be $d_{Au}$=0.0031" (0.0079 cm).

In yet another example, the appropriate diameter of nitinol monofilament wires to be braided with 0.0024" (0.0061 cm) outer diameter 1×7 stranded tungsten wire (constructed from a central monofilament of tungsten surrounded by a ring of 6 tungsten monofilaments of the same diameter as the central filament) into tubular braided mesh having uniform pore size is calculated as follows. The equations above are used to calculate EI for each individual tungsten filament (having a filament diameter of 0.0008" (0.002 cm) in this example). The EI of the stranded wire is approximated as seven times that of one tungsten monofilament (assuming the friction between filaments is small compared to the bending stiffness of the filaments, therefore no adjustment is made for friction). The equations above are solved for $d_{NiTi}$ by equating EI for the nitinol wire with the calculated EI for the tungsten stranded wire. In this example $d_{NiTi}$ is approximately equal to 0.0047" (0.012 cm). It is understood that improved calculations for the stiffness of multifilament wire can be employed as part of these calculations. Improved calculations may account for frictional forces between strands, non-linear configuration of some or all of the strands, or other factors.

Another means for achieving uniform pore size braided mesh comprised of some radiopaque wires is by matching radiopaque and non-radiopaque wire diameters. The smaller the distance between interwoven radiopaque and non-radiopaque wires the greater the variation in pore size caused by differing wire diameters. In a preferred embodiment of the device, the largest diameter of wires used in the device is no more than 5 times the smallest diameter of wires used in the device. In a more preferred embodiment of the device, the largest diameter of wires used in the device is no more than 4 times the smallest diameter of wires used in the device. In a further preferred embodiment of the device, the largest diameter of wires used in the device is no more than 2 times the smallest diameter of wires used in the device. In a further preferred embodiment of the device, the largest diameter of wires used in the device is no more than 1.5 times the smallest diameter of wires used in the device. In a most preferred embodiment both the wire diameter and the wire stiffness of both the radiopaque and non-radiopaque wires are similar.

A method of using a device made from the inventive mesh is as follows. An embolic protection device, made using methods similar to those discussed in connection with FIG. 2, is delivered percutaneously to a region of interest in the body of a patient using methods known in the art. Optionally a catheter is used to deliver the filter to the region of interest. Fluoroscopy is used by the operator to visualize the mouth and the body of the filter to ascertain that the filter is positioned appropriately in relation to a treatment or diagnostic site, for example, positioned such that the mouth of the filter is distal to a stenosis in an artery, and also by example, positioned such that the body of the filter is in a healthy region of vessel suitable for use as a landing zone for the filter. The filter is then deployed and the catheter (if used) is removed from the vicinity of the filter. The operator uses fluoroscopy to ascertain that the mouth of the filter is adequately deployed against the vessel wall with no gaps, distal to the lesion, and proximal to any important side branch vessels. Radiopaque contrast media may be injected at this time or at any time to assist with visualization of the patient's anatomy. The treatment site is treated, for example by dilating a lesion with a balloon dilatation catheter and by deploying a stent or drug eluting stent at the treatment site, although other methods known in the art can be used.

After or during treatment or both, the operator may visualize the mouth and body of the device and may adjust the position of the device to assure, for example, that the device is properly located along the length of the vessel and properly apposed to the vessel wall. After treatment the device is recovered. Optionally a catheter is used during the recovery process. At least a portion of the filter is drawn into the recovery catheter (if used) and the mouth and body of the filter are observed under fluoroscopy to ascertain when the device is sufficiently drawn into the catheter. If difficulty is encountered while drawing the filter into the catheter the devices are again imaged under fluoroscopy and the cause of the difficulty is diagnosed in part by observing the radiopaque portions of the device. The filter (and recovery catheter if used) are then withdrawn from the vessel. If resistance to withdrawal is encountered then the devices are imaged under fluoroscopy and the cause of resistance is determined and eliminated.

While this document has described an invention mainly in relation to braided tubular mesh used for embolic protection filtering devices used in arteries, it is envisioned that the invention can be applied to other conduits in the body as well including veins, bronchi, ducts, ureters, urethra, and other lumens intended for the passage of air, fluids, or solids. The invention can be applied to other devices such as vena cava filters, stents, septal defect closure devices, and other devices comprised of mesh having the benefits described above.

While the various embodiments of the present invention have related to embolic protection filtering devices, the scope of the present invention is not so limited. Further, while choices for materials and configurations have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A stent comprising a mesh, the mesh comprising at least one radiopaque strand and at least one non-radiopaque strand, the at least one radiopaque strand and the at least one non-radiopaque strand each having different cross-sectional dimensions, and wherein each of the strands has an index of wire stiffness EI, where EI is the mathematical product of the Young's modulus (E) and the second moment of area (I), and wherein the EI of each non-radiopaque strand is no more than five times the EI of a strand having the smallest EI of any of the strands.

2. The stent of claim 1, wherein the mesh is self-expanding.

3. The stent of claim 1, wherein the mesh is tubular.

4. The stent of claim 3, wherein the mesh is braided.

5. The stent of claim 1, wherein each strand has a round cross-section.

6. The stent of claim 5, wherein the mesh comprises only two types of strands, a first type comprising the at least one radiopaque strand and having a cross-sectional dimension D1 and a second type comprising the at least one non-radiopaque strand and having a cross-sectional dimension D2, wherein the cross-sectional dimension D2 is greater than the cross-sectional dimension D1.

7. The stent of claim 1, wherein the Young's modulus of the at least one radiopaque strand and the Young's modulus of the at least one non-radiopaque strand differ by 20 percent or more.

8. The stent of claim 1, wherein the EI of each of the strands is no more than four times the EI of a strand having the smallest EI of any of the strands.

9. The stent of claim 1, wherein the mesh comprises pores and when the mesh is at rest in free space no pore has an area more than 1.2 times the mesh pore size, the mesh pore size being the average area of five pores serially adjacent to the pore.

10. The stent of claim 1, wherein the at least one first strand is an alloy of platinum and tungsten and the at least one second strand comprises nickel.

11. The stent of claim 1, wherein the largest cross-sectional dimension of a strand is no more than 1.5 times the smallest cross-sectional dimension of any other strand.

12. A stent comprising a mesh, the mesh comprising at least one radiopaque strand and at least one non-radiopaque strand, the at least one radiopaque strand and the at least one non-radiopaque strand each having different cross-sectional dimensions, and wherein each of the strands has an index of wire stiffness EI, where EI is the mathematical product of the Young's modulus (E) and the second moment of area (I), and wherein the EI of each non-radiopaque strand is no more than five times the EI of each radiopaque strand.

13. The stent of claim 12, wherein each strand has a round cross-section.

14. The stent of claim 13, wherein the mesh comprises only two types of strands, a first type comprising the at least one radiopaque strand and having a cross-sectional dimension D1 and a second type comprising the at least one non-radiopaque strand and having a cross-sectional dimension D2, wherein the cross-sectional dimension D2 is greater than the cross-sectional dimension D1.

15. The stent of claim 12, wherein the Young's modulus of the radiopaque strand and the Young's modulus of the non-radiopaque strand differ by 20 percent or more.

16. The stent of claim 12, wherein the mesh comprises more non-radiopaque strands than radiopaque strands.

17. The stent of claim 12, wherein the EI of each of the strands is no more than four times the EI of a strand having the smallest EI of any of the strands.

18. The stent of claim 12, wherein the mesh comprises pores and when the mesh is at rest in free space no pore has an area more than 1.2 times the mesh pore size, the mesh pore size being the average area of five pores serially adjacent to the pore.

19. The stent of claim 12, wherein the at least one radiopaque strand is an alloy of platinum and tungsten and the at least one non-radiopaque strand comprises nickel.

20. The stent of claim 12, wherein the largest cross-sectional dimension of a strand is no more than 1.5 times the smallest cross-sectional dimension of any other strand.

21. A stent comprising a mesh, the mesh comprising at least one radiopaque strand and at least one non-radiopaque strand, the at least one radiopaque strand and the at least one non-radiopaque strand each having different cross-sectional dimensions, and wherein each of the strands has an index of wire stiffness EI, where EI is the mathematical product of the Young's modulus (E) and the second moment of area (I), and wherein the EI of each radiopaque strand is no more than five times the EI of a strand having the smallest EI of any of the strands.

22. The stent of claim 21, wherein the mesh is self-expanding.

23. The stent of claim 21, wherein the mesh is tubular.

24. The stent of claim 23, wherein the mesh is braided.

25. The stent of claim 21, wherein each strand has a round cross-section.

26. The stent of claim 25, wherein the mesh comprises only two types of strands, a first type comprising the at least one radiopaque strand and having a cross-sectional dimension D1 and a second type comprising the at least one non-radiopaque strand and having a cross-sectional dimension D2, wherein the cross-sectional dimension D2 is greater than the cross-sectional dimension D1.

27. The stent of claim 21, wherein the Young's modulus of the at least one radiopaque strand and the Young's modulus of the at least one non-radiopaque strand differ by 20 percent or more.

28. The stent of claim 21, wherein the EI of each of the at least one non-radiopaque strand is no more than four times the EI of any radiopaque strand.

29. The stent of claim 21, wherein the mesh comprises pores and when the mesh is at rest in free space no pore has an area more than 1.2 times the mesh pore size, the mesh pore size being the average area of five pores serially adjacent to the pore.

30. The stent of claim 21, wherein the at least one radiopaque strand is an alloy of platinum and tungsten and the at least one non-radiopaque strand comprises nickel.

31. The stent of claim 21, wherein the cross-sectional dimension of the at least one non-radiopaque strand is no more than 1.5 times the cross-sectional dimension of the at least one radiopaque strand.

\* \* \* \* \*